United States Patent [19]

Curatolo et al.

[11] Patent Number: 5,605,889
[45] Date of Patent: Feb. 25, 1997

[54] METHOD OF ADMINISTERING AZITHROMYCIN

[75] Inventors: William J. Curatolo, Niantic; George H. Foulds, Waterford, both of Conn.; Hylar L. Friedman, Brattleboro, Vt.

[73] Assignee: Pfizer Inc., New York, N.Y.

[21] Appl. No.: 235,069

[22] Filed: Apr. 29, 1994

[51] Int. Cl.$^6$ .................. A61K 31/70; A61K 9/14; A61K 9/20
[52] U.S. Cl. ................. 514/29; 514/960; 424/464; 424/465; 424/474; 424/480; 424/481; 536/7.2
[58] Field of Search ............... 514/29, 960; 536/7.2; 424/464, 465, 474, 480, 481

[56] References Cited

U.S. PATENT DOCUMENTS

| | | | |
|---|---|---|---|
| 4,382,085 | 5/1983 | Sciavolino et al. | 514/29 |
| 4,474,768 | 10/1984 | Bright | 514/29 |
| 4,517,359 | 5/1985 | Kobrehel et al. | 536/7.4 |
| 4,963,531 | 10/1990 | Remington | 514/29 |
| 5,250,518 | 10/1993 | Kobrehel et al. | 514/29 |
| 5,350,839 | 9/1994 | Asaka et al. | 536/7.4 |

FOREIGN PATENT DOCUMENTS

| | | |
|---|---|---|
| 0307128 | 3/1989 | European Pat. Off. |
| 0582396 | 2/1994 | European Pat. Off. |

OTHER PUBLICATIONS

Curatolo et al. *J. Pharm. Sci.*, vol. 77 (4), pp. 322–324, (1988).
Welling et al. *J. Pharm. Sci.*, vol. 67 (6), pp. 764–766, (1978).
Welling et al. *J. Pharm. Sci.*, vol. 68 (2), pp. 150–155, (1979).
Malmborg, A. *Curr. Med. Res. Opin.* vol. 5 (Suppl. 2), pp. 15–18, (1978).
Drew et al., Pharmacotherapy, 12, 3, 161–173 (1992).
Chu et al., J. Clin. Pharmacol., 32, 32–36 (1992).
Hopkins, S., Am. J. Med., 91 (Suppl 3A), 40S–45S (1991).
Toothaker et al., Ann. Rev. Pharmacol. Toxicol. vol. 20, 173–199, 1980.
Russell et al., Pharmaceutical Research, vol. 10, No. 2, 187–196, 1993.
CA Abstracts: vol. 120:38194a; 1994.
Zithromax (Trademark of Pfizer, Inc.) Capsules Package Insert for azithromycin capsule dosage form sold commercially in U.S.

*Primary Examiner*—John Kight
*Assistant Examiner*—Howard C. Lee
*Attorney, Agent, or Firm*—Peter C. Richardson; Gregg C. Benson; James T. Jones

[57] ABSTRACT

An oral dosage form of azithromycin which does not exhibit an adverse food effect; Specific azithromycin oral dosage forms including tablets, powders for oral suspensions and unit dose packets; Methods of treating microbial infections with the dosage forms; And therapeutic packages containing the dosage forms.

99 Claims, No Drawings

METHOD OF ADMINISTERING AZITHROMYCIN

This invention relates to a dosage form of azithromycin, and also to a method of treating a microbial infection which involves administering azithromycin in the fed state to a mammal, including a human patient, in need of such treatment.

BACKGROUND OF THE INVENTION

Azithromycin is the U.S.A.N. (generic name) for 9a-aza-9a-methyl-9-deoxo-9a-homoerythromycin A, a broad spectrum antimicrobial compound derived from erythromycin A. Azithromycin was independently discovered by Bright, U.S. Pat. No. 4,474,768 and Kobrehel et al., U.S. Pat. No. 4,517,359. These patents disclose that azithromycin and certain derivatives thereof possess antibacterial properties and are accordingly useful as antibiotics.

In general, it is known that the absorption and bioavailability of any particular therapeutic agent can be affected by numerous factors when dosed orally. Such factors include the presence of food in the gastrointestinal (GI) tract because, in general, the gastric residence time of a drug is usually significantly longer in the presence of food than in the fasted state. If the bioavailability of a drug is affected beyond a certain point due to the presence of food in the GI tract, the drug is said to exhibit a "food effect". Food effects are important inasmuch as, when a drug exhibits an adverse food effect, there is risk associated with administering it to a patient who has eaten recently. The risk derives from the potential that absorption into the bloodstream may be adversely affected to the point that the patient risks insufficient absorption to remediate the condition for which the drug was administered.

Other factors can also be involved in drug bioavailability, the following being a non-comprehensive listing:

(1) The particular dosage form can affect bioavailability. For example, the gastric residence time of a tablet or capsule can be significantly longer than that of a suspension, and the difference may vary depending on whether the subject has eaten or is fasted.

(2) The pH of the stomach varies, between the fed and fasted state, with the amount of food therein, and drugs which are decomposition-sensitive to pH can be affected accordingly.

(3) The capacity of the liver to metabolize an absorbed drug (so-called "first pass" metabolism) may vary with the type of meal eaten. For example some vegetables (such as brussels sprouts) can stimulate first pass metabolism of some drugs, but not others. Grapefruit juice, on the other hand, may inhibit first pass metabolism of some drugs.

(4) Bile, which is released from the gallbladder into the small intestine when a meal is ingested, has the ability to solubilize poorly soluble drugs and thus increase bioavailability.

Additional factors can also be involved in the absorption and bioavailability of a particular drug, and absorption can actually be increased as well as decreased. These additional factors include, for example, pH-dependent solubility, site-specific intestinal permeation rate, instability to intestinal enzymes, susceptibility to first pass metabolism, and instability to colonic bacteria. Given the plethora of factors which can influence bioavailability, there usually is no way to predict, in the absence of actual testing, whether a particular drug will exhibit a food effect. For example, Toothaker and Welling, Ann. Rev. Pharmacol. Toxicol., 1980, 173–99, discuss various drugs whose absorption is delayed in the presence of food (cephalexin, cefaclor, metronidazole, aspirin, alclofenac, indoprofen, digoxin, cimetidine), whose absorption may be unaffected by food (ampicillin, erythromycin estolate, spiramycin, propylthiouracil, oxazepam, bendroflumethiazide), and whose absorption is increased in the presence of food (erythromycin ethylsuccinate, nitrofurantoin, 8-methoxsalen, propranolol, metoprolol, dicoumarol, diazepam, hydrochlorothiazide).

As a further example, there appears to be no clear or definitive support for the proposition that tablets might exhibit fewer food effects than capsules, or vice-versa. Toothaker and Welling review studies which demonstrate food related reduced absorption for tablet dosage forms of erythromycin stearate, aspirin, nafcillin, and sotalol.

In the case of azithromycin, at least one (unpublished) study has shown that the absorption of azithromycin can be adversely affected if the patient is in a fed state, and it has heretofore been conventional wisdom that azithromycin capsule dosage forms exhibit a so-called adverse "food effect". Accordingly, in countries where azithromycin is currently available for use in the treatment of human patients, the product is sold with the specific direction that it be administered only in the fasted state, i.e. at least one hour before or two hours following a meal.

It would accordingly be useful if azithromycin could be administered to patients that have eaten recently and also if a dosage form for azithromycin were available which could be administered to patients that have eaten, as well as patients in a fasted state.

SUMMARY OF THE INVENTION

This invention provides an oral dosage form of azithromycin which can be administered to a mammal (including humans) that has eaten and which exhibits substantially no adverse food effect, excluding any dosage form which contains a significant amount of an alkaline earth oxide or hydroxide. The dosage form exhibits a mean $(AUC_{fed})/(AUC_{fst})$ of at least 0.80 with a lower 90% confidence limit of at least 0.75, the terms "$(AUC_{fed})/(AUC_{fst})$" and "90% confidence limit" being fully defined below.

In a further aspect, this invention provides a specific oral azithromycin dosage form which does not exhibit an adverse food effect. The dosage form comprises azithromycin and a pharmaceutically acceptable carrier, as hereinafter further detailed and described. The dosage form is in the form of a tablet (including both swallowable-only and chewable forms), in the form of a unit dose packet (sometimes referred to in the art as a "sachet"), in the form of a suspension made from a unit dose packet, in the form of a powder for oral suspension, and in the form of an oral suspension per se. It is noted that when a unit dose packet is constituted, it is probably mainly in the form of a suspension if reconstituted according to directions, although the extent of suspension versus solution depends on a number of factors such as pH. The use of the term "suspension" herein is intended to embrace liquids containing azithromycin partially in suspension and partially in solution, and also totally in solution.

In a further aspect, this invention provides a method for treating a microbial infection in a mammal which comprises administering, to a mammal that has eaten in need of such treatment, an antimicrobially effective amount of azithromycin in an oral dosage form which exhibits substantially no adverse food effect. The dosage form employed exhibits a mean $(AUC_{fed})/(AUC_{fst})$ of at least 0.80 with a lower 90% confidence limit of at least 0.75.

Reference herein and in the claims to a mammal (including humans) that has "eaten" means that the mammal has eaten food of any sort within one hour prior to dosing up to two hours after dosing.

In a further aspect, this invention provides a therapeutic package suitable for commercial sale, comprising a container, an oral dosage form of azithromycin which does not exhibit an adverse food effect contained therein, and, associated with said container, written matter non-limited as to whether the dosage form can be taken with or without food.

It is noted that powders for oral suspension and unit dose packets, of course, are not ingested directly by patients; rather, they are reconstituted in a suitable vehicle. These terms are nonetheless considered to be within the penumbra of the term "dosage form" for purposes of this invention.

Capsules as a dosage form do not form a part of the invention.

For purposes of this invention azithromycin may be administered alone or in combination with other therapeutic agents.

A food effect can be detected and quantified as described, for example in Toothaker and Welling, supra, by determining the area under a curve (AUC) which plots the serum concentration (e.g., in µg/mL) of azithromycin along the ordinate (Y-axis) against time along the abscissa (X-axis). Generally, the values for AUC represent a number of values taken from all the subjects in a patient test population and are, therefore, mean values averaged over the entire test population. By measuring the area under the curve for a fed population of subjects ($AUC_{fed}$) and comparing it with the area for the same population of fasted subjects ($AUC_{fst}$), it can be determined whether a given drug exhibits an adverse food effect or not.

For definitional purposes of this invention, and specifically with respect to azithromycin dosage forms only, a dosage form of azithromycin exhibits an adverse food effect if, after dosing a population, once fasted and once fed, the mean $(AUC_{fed})/(AUC_{fst})$ is below the value 0.80 and/or the lower 90% confidence limit for this ratio is below 0.75.

Conversely, a dosage form of azithromycin which does not exhibit an adverse food effect is one which, when tested on a test population, exhibits a value for $(AUC_{fed})/(AUC_{fst})$ of at least 0.80 and a lower 90% confidence limit for this value of at least 0.75. The value for mean $(AUC_{fed})/(AUC_{fst})$ can have any value above 0.80 and still be within the scope of this invention, though it is preferred that it have an upper (mean) limit of 1.25, with an upper 90% confidence limit of 1.40 or below.

A population of "fed" subjects, for purposes of definition and for measuring $AUC_{fed}$, is one made up of subjects each of whom has eaten a Food and Drug Administration (FDA)-recommended standard high fat breakfast within a period of twenty minutes, and then ingested (i.e., swallowed) the test dosage form essentially immediately thereafter. A standard high-fat breakfast consists of, for example, two eggs fried in one tablespoon of butter, two strips of bacon, six ounces of hash brown potatoes, two pieces of toast with two teaspoons of butter and two pats of jelly, and eight ounces of whole milk. This standard high-fat breakfast contains approximately 964 calories, 54% supplied as fat (58 gm) and 12% supplied as protein, calculated using the monograph "Nutritive Value of Foods", U.S. Department of Agriculture Home and Garden Bulletin Number 72. Additional food can also be consumed within the twenty minute period and the subject still qualifies as "fed". A "fasted subject" for purposes of definition and for measuring $AUC_{fst}$ is one who has not eaten for at least eight hours, typically overnight, prior to ingestion of the dosage form.

The 90% confidence limits on $AUC_{fed}/AUC_{fst}$ for a particular population, in this case either a fed or a fasted population, can be (and were) calculated as described following using Schuirman's two one-sided test procedure.

The log-transformed AUCs were analyzed by means of an analysis of variance appropriate for a two-period, two-treatment crossover design. Analysis was carried out using Statistical Analysis System (SAS) software from SAS Institute, Cary, N.C. SAS procedure referred to in the SAS software as PROC GLM was used to determine sequence, subject within sequence, period and treatment (Fed/Fasted) effects. The sequence effect was tested using the [subject within sequence] mean square from the analysis of variance (ANOVA) as an error term. All other effects were tested against residual error (error mean square) from the ANOVA. The LSMEANS statement of SAS was used to calculate the least square means and their standard errors and covariances. These were used to obtain estimates for adjusted differences between treatment means and standard errors associated with these differences (log transformed).

The 90% confidence interval for two-way crossover design was constructed, based on these estimates, as the difference plus (or minus) the standard error of the difference times the 95th percentile of the t-distribution with (twice the sample size-2) degrees of freedom. The anti-log was taken on the limits to obtain the corresponding confidence for the ratio.

That a dosage form according to the invention does not exhibit an adverse food effect is surprising in view of the fact that azithromycin is unstable at low (acid) pH, on the order of the acidity encountered at the pH of stomach acid. The inventors have demonstrated that azithromycin breaks down if exposed to stomach juices which inherently exhibit acid pH. Thus, without being bound to any mechanism of action, it is surprising that rapid disintegration in the GI tract appears to be of importance to the invention.

Commonly assigned co-pending application Ser. No. 07/922,262 filed Jul. 30, 1992 discloses taste masking compositions of bitter pharmaceutical agents, such as azalide antibiotics, containing, as a taste-masking component, a basic compound selected from the group consisting of alkaline earth oxides and alkaline earth hydroxides. A composition of this invention, if it contains an alkaline earth oxide or hydroxide at all, contains less than a taste-masking amount of the taste-masking component. A composition of this invention therefore preferably contains less than about 1% of an alkaline earth oxide or hydroxide, and may be free of such taste-masking component entirely.

DETAILED DESCRIPTION

Azithromycin is typically present in formulations according to the invention in an amount of from about 25 mg to about three grams, preferably 250 mg to two grams, for treatment of a human. If dosage forms are to be used for animal/veterinary applications, the amount can, of course, be adjusted to be outside these limits depending, for example, on the size of the animal subject being treated (e.g., a horse). The term "azithromycin" includes the pharmaceutically acceptable salts thereof, and also anhydrous as well as hydrated forms. The azithromycin is preferably present as the dihydrate, disclosed, for example, in published European Patent Application 0 298 650 A2.

In order to test whether a particular azithromycin dosage form exhibits an adverse food effect, the most reliable method is actually to test the dosage form in vivo on a subject population, once fed and once fasted, determine the level of serum (or plasma) azithromycin with time, plot curves for the concentration of serum (or plasma) azithromycin with time in each subject (fed and fasted) as described above, determine the area under each curve (conventionally, for example by simple integration) and finally determine whether the mean ratio $(AUC_{fed})/(AUC_{fst})$ exceeds 0.80, and whether the lower 90% confidence limit equals or exceeds 0.75.

It is believed that the azithromycin dosage forms of the invention do not exhibit a food effect in large part because they either provide azithromycin ready for dissolution in the GI tract essentially immediately following ingestion (suspensions), or they disintegrate rapidly following ingestion (tablets) and thereby provide azithromycin rapidly for dissolution. While not wishing to be bound by theory, it is believed that if an azithromycin dosage form provides azithromycin immediately following ingestion for dissolution in the GI tract, or at least provides azithromycin for dissolution within a certain time period following ingestion, the azithromycin will be absorbed into the bloodstream at a rate which results in substantially no adverse food effect. In order for an adequate rate of absorption to occur, it is believed that the dosage form should provide azithromycin at a rate such that at least about 90% of the azithromycin dissolves within about 30 minutes following ingestion, preferably within about 15 minutes following ingestion. A non-capsule dosage form comprising azithromycin is also considered to fall within the scope of the appended claims if it satisfies the in vitro dissolution testing requirements enumerated herein. An azithromycin dosage form according to the invention exhibits at least about 90% dissolution of azithromycin within about 30 minutes, preferably within 15 minutes, when an amount of the dosage form equivalent to 200 mg of azithromycin is tested as set forth in USP test <711> in a USP-2 dissolution apparatus under conditions at least as stringent as the following: 900 ml approx. 0.1M dibasic sodium phosphate buffer, pH 6.0, 37° C. with paddles turning at 100 rpm. This test is described in US Pharmacopaea XXII, pp. 1578–1579. Dosage forms which pass this test under more stringent conditions (lower volume of buffer, greater amount of dosage form, lower temperature, higher pH, lower paddle speed) are also included under the above definition. Any modifications to this test are also described herein. The time required for dissolution of a particular azithromycin dosage form in this in vitro test is believed to be an indicator of the time required for dissolution of the dosage form in the GI environment. The following discussion is believed pertinent in this regard.

It is generally assumed and observed that the in vitro dissolution rate of dosage forms exhibits a rank order correlation with in vivo dissolution, particularly for a single dosage form type, e.g. tablets, which vary systematically in composition. Thus in vitro dissolution evaluation serves an important role in control of the quality of manufactured dosage forms. It is not necessarily true that the in vitro dissolution rate is exactly the same as the in vivo dissolution rate. This is not surprising, since the artificial conditions of an in vitro dissolution test (e.g. vessel geometry, stirring rate, stirring method, and so forth) are not identical to the conditions under which a dosage form disintegrates and dissolves in the GI tract.

When comparing dosage forms of different type, e.g. capsules and tablets, in vitro dissolution rate should correlate roughly with in vivo dissolution rate. However, subtle differences exist between the disintegration mechanisms of capsules and tablets. For capsules, at least partial dissolution of the gelatin shell must precede complete dissolution of the enclosed drug. Furthermore, capsule shells generally dissolve first at the capsule ends, and later at the capsule center. Tablets, on the other hand, disintegrate homogeneously. Thus subtle differences may exist in the in vitro/in vivo dissolution correlation when comparing capsules and tablets. For example, capsules and tablets which exhibit similar in vitro dissolution rates may exhibit subtle differences in in vivo dissolution rate. While such subtle differences may have no therapeutically significant effect on systemic bioavailability of an orally dosed drug, there are situations in which a significant effect may occur. For example, if a drug has the potential to exhibit an adverse food effect, drug-containing capsules and tablets which exhibit similar in vitro dissolution rates may actually differ with respect to whether an adverse food effect is observed when the dosage forms are orally dosed. In fact, this has been observed for azithromycin, as exemplified in the Examples herein.

For the in vitro dissolution studies disclosed herein, azithromycin was assayed by HPLC, utilizing a 5 micron alumina based hydrocarbonaceous spherical particle chromatographic column (15 cm×0.4 cm), and a 5 micron alumina based hydrocarbonaceous spherical particle precolumn (5 cm×0.4 cm) (both available from ES Industries, Marlton, N.J.). A mobile phase consisting of 71% phosphate buffer/29% acetonitrile (pH 11) was used, with electrochemical detection (e.g. Bioanalytical Systems, West Lafayette, Ind., LC-4B amperometric detector with dual series glassy carbon electrodes).

For in vivo food effect studies, serum azithromycin is assayed using an HPLC assay described by R. M. Shepard et al. (1991) J. Chromatog. Biomed. Appl. 565, 321–337, with amperometric electochemical detection. Alternatively, any assay method that produces equivalent results, for example, bioassay, can be used.

Tablets according to the invention contain, as necessary ingredients, azithromycin and a disintegrant. Examples of tablet disintegrants are starch, pregelatinized starch, sodium starch glycolate, sodium carboxymethylcellulose, crosslinked sodium carboxymethylcellulose (sodium croscarmellose; crosslinked starch available under the registered trademark Ac-Di-Sol from FMC Corp., Philadelphia, Pa.), clays (e.g. magnesium aluminum silicate), microcrystalline cellulose (of the type available under the registered trademark Avicel from FMC Corp. or the registered trademark Emcocel from Mendell Corp., Carmel, N.Y.), alginates, gums, surfactants, effervescent mixtures, hydrous aluminum silicate, cross-linked polyvinylpyrrolidone (available commercially under the registered trademark PVP-XL from International Specialty Products, Inc.), and others as known in the art. Preferred disintegrants for azithromycin tablets are sodium croscarmellose (Ac-Di-Sol), sodium starch glycolate (available commercially under the registered trademarks Primojel from Avebe (Union, N.J.) or Generichem, (Little Falls, N.J.) and Explotab from Mendell Corp.), microcrystalline cellulose (Avicel), and cross-linked polyvinylpyrrolidone (PVP-XL). Azithromycin tablets of this invention comprise azithromycin and 1–25% disintegrant, preferably 3–15% disintegrant based on total tablet weight. For example, a 463.5 mg tablet (250 mg activity azithromycin) may contain 9 mg sodium croscarmellose and 27 mg pregelatinized starch.

In addition to the active ingredient azithromycin and a disintegrant, tablets according to this invention may be formulated to optionally include a variety of conventional excipients, depending on the exact formulation, such as binders, flavorings, buffers, diluents, colors, lubricants, sweetening agents, thickening agents, and glidants. Some excipients can serve multiple functions, for example as both binder and disintegrant.

Examples of binders are acacia, cellulose derivatives (such as methylcellulose and carboxymethylcellulose, hydroxypropylmethylcellulose, hydroxypropylcellulose, hydroxyethylcellulose), gelatin, glucose, dextrose, xylitol, polymethacrylates, polyvinylpyrrolidone, starch paste, sucrose, sorbitol, pregelatinized starch, gum tragacanth, alginic acids and salts thereof such as sodium alginate, magnesium aluminum silicate, polyethylene glycol, guar gum, bentonites, and the like. A preferred binder for azithromycin tablets is pregelatinized starch (available, for example, under the registered trademark Starch 1500, from Colorcon, Inc., West Point, Pa.).

Flavors incorporated in the composition may be chosen from synthetic flavor oils and flavoring aromatics and/or natural oils, extracts from plants leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Generally the flavoring will be present in an amount of from 0.5 to about 3.0 percent by weight based on the total tablet weight, when a flavor is used.

A variety of materials may be used as fillers or diluents. Examples are spray-dried or anhydrous lactose, sucrose, dextrose, mannitol, sorbitol, starch (e.g. starch 1500), cellulose (e.g. microcrystalline cellulose; Avicel), dihydrated or anhydrous dibasic calcium phosphate (available commercially under the registered trademark Emcompress from Mendell or A-Tab and Di-Tab from Rhone-Poulenc, Inc., Monmouth Junction, N.J.), calcium carbonate, calcium sulfate, and others as known in the art.

Lubricants can also be employed herein in the manufacture of certain dosage forms, and will usually be employed when producing tablets. Examples of lubricants are magnesium stearate, stearic acid, glycerylbehaptate, polyethylene glycol, ethylene oxide polymers (for example, available under the registered trademark Carbowax from Union Carbide, Inc., Danbury, Conn.), sodium lauryl sulfate, magnesium lauryl sulfate, sodium oleate, sodium stearyl fumarate, DL-leucine, colloidal silica, and others as known in the art. Preferred lubricants are magnesium stearate, and mixtures of magnesium stearate with sodium lauryl sulfate. Lubricants generally comprise 0.5 to 7.0% of the total tablet weight.

Other excipients such as glidants and coloring agents may also be added to azithromycin tablets. Coloring agents may include titanium dioxide and/or dyes suitable for food such as those known as F. D. & C, dyes and natural coloring agents such as grape skin extract, beet red powder, beta carotene, annato, carmine, turmeric, paprika, and so forth. A coloring agent is an optional ingredient in the compositions of this invention, but when used will generally be present in an amount up to about 3.5 percent based on the total tablet weight.

As known in the art, tablet blends may be dry-granulated or wet granulated before tableting. Alternatively, tablet blends may be directly compressed. The choice of processing approach depends upon the properties of the drug and chosen excipients, for example particle size, blending compatibility, density and flowability. For azithromycin tablets, granulation is preferred, with wet granulation being most preferred. Azithromycin may be wet-granulated, and then other excipients may be added extragranularly. Alternatively, azithromycin and one or more excipients may be wet-granulated. In addition, tablets may also be coated, with a coating that exhibits little or no effect on or interference with tablet dissolution, to assure ease of swallowing or to provide an elegant appearance.

In a preferred embodiment, tablets of this invention are film-coated to provide ease of swallowing and an elegant appearance. Many polymeric film-coating materials are known in the art. A preferred film-coating material is hydroxypropylmethylcellulose (HPMC). HPMC may be obtained commercially, for example from Colorcon Corp., in coating formulations containing excipients which serve as coating aids, under the registered trademark Opadry. Opadry formulations may contain lactose, polydextrose, triacetin, polyethyleneglycol, polysorbate 80, titanium dioxide, and one or more dyes or lakes. Other suitable film-forming polymers also may be used herein, including, hydroxypropylcellulose, and acrylate-methacrylate copolymers.

The tableting process itself is otherwise standard and readily practiced by forming a tablet from a desired blend or mixture of ingredients into the appropriate shape using a conventional tablet press. Tablet formulation and conventional processing techniques have been widely described, for Example in *Pharmaceutical Dosage Forms: Tablets;* Edited By Lieberman, Lachman, and Schwartz; Published by Marcel Dekker, Inc., 2d Edition, Copyright 1989, the text of which is herein incorporated by reference.

The azithromycin dosage forms of this invention also include powders to make oral suspensions, and also the oral suspensions themselves. Generally the powder is a non-caking, free flowing powder which is sold direct to pharmacies or other retail outlets and then made up into the actual suspension by a pharmacist. The oral suspension is thus the actual dosage form ingested by patients. The typical shelf life for a suspension is about five days because azithromycin therapy is generally of five days duration.

Azithromycin suspensions according to the invention contain, as necessary ingredients in addition to azithromycin, one or more thickening agents in a total amount of 0.1 to 2%, and a buffer or pH-altering agent in an amount of 0.1 to 2.5%, with percentages being based on the weight of the dry powder formulation. Dispersing agents may also be used in an amount of from 0.05 to 2%. Preservatives may also be used in an amount from 0.1 to 2%.

Suitable thickening agents function as suspending agents and include, for example, hydrocolloid gums known for such purpose, examples of which include xanthan gum, guar gum, locust bean gum, gum tragacanth, and the like. Alternatively, synthetic suspending agents may be used such as sodium carboxymethylcellulose, polyvinylpyrrolidone, hydroxypropylcellulose and the like.

Dispersing agents include colloidal silicon dioxide, available from Cabot Corporation, Boston, Mass. under the trade designation Cab-O-Sil.

For the purpose of preparing formulations of a powder for oral suspension, the bitter taste of azithromycin may be masked by including a basic buffer or pH-altering agent which will provide a pH of approximately 10 in the constituted suspension. Maintenance of the pH at around 10 minimizes the quantity of azithromycin in solution, and thus masks the bitter taste of the drug. Many combinations of flavors or flavor systems may be used in addition to mask the bitter taste of azithromycin. Preferred flavors are those which provide a constant flavor for approximately 5 days at the elevated pH of the formulation after constitution. A preferred flavor system consists of spray dried cherry #11929, artificial creme de vanilla #11489, and spray-dried artificial banana #15223 available commercially from Bush Boake Allen, Inc., Chicago, Ill. Artificial sweeteners may also be used.

A powder used to make a suspension herein may also contain conventional optional ingredients such as (1) wetting agents such as sorbitan monolaurate, polysorbate 80, and sodium lauryl sulfate; (2) anti-foaming agents and (3) sweeteners and fillers such as glucose. The powder may also contain a buffer to maintain a high pH upon reconstitution, as discussed above. Suitable buffers and pH-altering agents include anhydrous tribasic sodium phosphate, anhydrous sodium carbonate, glycine, and the like. Suitable preservatives are well known, for example sodium benzoate and the like. After swallowing, azithromycin from a suspension dissolves quickly.

In the preparation of azithromycin powder for oral suspension formulations, all ingredients may be blended together and deagglomerated, as known in the art. Preferably, azithromycin and flavors are blended, and other ingredients are separately blended. Finally, these two blends are blended and deagglomerated.

Preferred oral suspensions are those which resuspend easily after constitution with aqueous media and which do not cake on storage after constitution. Preferred suspensions contain sucrose NF, when sucrose is used, and anhydrous excipients when available, to assure facile suspension upon constitution. The drug-containing powder is generally reconstituted with water.

Suspensions of this invention exhibit about 90% dissolution of azithromycin in vitro in about 15 minutes. The test can be summarized as follows:

Shake the azithromycin-containing bottle to loosen the powder, and constitute the sample as per label instructions, e.g. as described in Example 12 to provide a 40 mg/ml azithromycin suspension. Shake the bottle vigorously for 2 minutes, then allow the bottle to sit for 30 minutes. Shake again vigorously for 15 seconds. Withdraw 5 ml from the bottle (typically equivalent to 200 mg of azithromycin), taking care to eliminate air bubbles. Carefully dispense the 5 ml aliquot of the azithromycin suspension approximately 10 cm over the surface of the dissolution medium (0.10M sodium phosphate buffer, pH 6.0) in a USP Apparatus 2, with the paddles positioned 2.5 cm from the bottom of the vessels. Begin rotating the paddles at 25 rpm, after the Oral Suspension samples have sunk to the bottom of the vessels. Remove approximately 10 ml from the dissolution vessel at each sampling time, filter, and assay flitrate for azithromycin using the HPLC assay described previously.

An azithromycin unit dose packet dosage form (also referred to herein as a "sachet") consists of a unit packet, designed to be emptied into an aqueous vehicle, for example water or a natural or artificial fruit beverage. The packet contains a blend of azithromycin and excipients which is thus reconstituted. The packet contains, as necessary ingredients, azithromycin and a dispersing agent which makes the sachet powder free flowing, for example colloidal silicon dioxide such as Cab-O-Sil from Cabot. Generally the dispersing agent is present in an amount of about 0.2 to 2.0% by weight based on the weight of the dry sachet as it is to be sold. The dispersing agent also serves as a glidant. The formulation may also optionally contain ingredients including (1) a filler or sweetener (e.g. glucose); (2) a buffer (e.g. sodium phosphate); (3) a wetting agent such as a surfactant, for example sodium lauryl sulfate, and (4) flavors such as any of those enumerated herein, and the like. The powder in the packet flows freely and disperses quickly, essentially immediately upon stirring when reconstituted. Azithromycin unit dose packet dosage forms may be prepared by blending and deagglomerating all ingredients, as known in the art. Preferably, the filler (e.g. sucrose), buffer (e.g. anhydrous tribasic sodium phosphate), and glidant (e.g. colloidal silicon dioxide) are blended and deagglomerated, followed by blending with azithromycin and flavors, followed by deagglomeration. The azithromycin in the packet dissolves quickly when evaluated as follows. The contents of a packet are added to a 250 ml beaker containing 60 ml water treated with the Milli-Q Plus system, Millipore Corp. (>18 megohms resistivity). The contents of the beaker are stirred with a spoon until a homogeneous suspension is obtained (1–2 min.). With the paddles raised, the suspension is poured into the center of a dissolution vessel of a USP-2 dissolution apparatus containing 900 ml 0.1M sodium phosphate buffer, pH 6.0. The paddles are then lowered into the vessel, and rotation is begun at 50 rpm. 10 mL aliquots are removed at each time point, filtered, and filtrates are assayed for azithromycin in solution, using an HPLC assay as described above. Using this method, greater than 90% dissolution of a 1 gm azithromycin packet is observed in less than 5 minutes. The packet thus does not exhibit an adverse food effect.

As stated, the oral azithromycin dosage forms disclosed and described above can be administered to a mammal, including man, in need of such treatment when the mammal has eaten, regardless of how recently and of the nature and quantity of food, without exhibiting an adverse food effect. To this end, and as an additional feature of the invention, this invention provides a therapeutic package suitable for commercial sale, comprising a container, an oral dosage form of azithromycin which does not exhibit an adverse food effect contained therein, and, associated with said package, written (i.e., printed) matter non-limited as to whether the dosage form can be taken with or without food. The written matter is of the type containing information and/or instructions for the physician, pharmacist or patient. The written material can be "non-limited as to whether the dosage form can be taken with or without food" by virtue of including no statement regarding whether or not the dosage form can be taken with or without food, i.e. the statement is silent with regard to food effects. Alternatively, the written material can be non-limited by containing one or more statements affirmatively informing the user (i.e., the patient, pharmacist, or physician) that the said oral dosage form can be taken by or administered to a patient regardless of whether the patient has eaten or otherwise imbibed food (optionally, for example, also stating something like "without regard to type or quantity of food"). The written material can not contain limiting language with respect to food, e.g, "This dosage form can not be taken with food" or "This dosage form may only be given after the patient has fasted" or the like.

The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual dosages for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

Printed or otherwise written matter is associated with the package in which the azithromycin dosage form is sold. The term "associated with" is intended to include all manners in which written matter, such as instructional or informational materials can be associated with a medicament, as known conventionally in the art. Thus written matter can be associated with the container, for example, by being: written on a label (e.g., the prescription label or a separate label) adhesively affixed to a bottle containing an azithromycin suspension; included inside a container as a written package insert, such as inside a box which contains unit dose packets; applied directly to the container such as being printed on the wall of a box; or attached as by being tied or taped, for example as an instructional card affixed to the neck of a bottle via a string, cord or other line, lanyard or tether type device. The written matter may be printed directly on a unit dose pack or blister pack or blister card. If the written matter affirmatively contains a non-limiting statement, the written matter may contain other information in addition. An affirmative non-limiting statement may, for example, read like the following exemplary statement:

This product does not exhibit an adverse food effect and may accordingly be administered to patients whether or not they have eaten and without regard to type or quantity of food.

or something similar, such as "may be taken without regard to food".

The invention will now be illustrated by the following examples which are not to be taken as limiting. In general, the examples demonstrate that (1) azithromycin capsules exhibit an adverse food effect, and that more slowly dissolving capsules exhibit a larger food effect, and (2) azithromycin fast dissolving tablet, powder for oral suspension, and unit dose packet dosage forms do not exhibit an adverse food effect.

EXAMPLE 1

This example is comparative and demonstrates the effect of a high fat breakfast on systemic exposure of azithromycin dosed in a capsule dosage form with moderate dissolution rate.

Capsules were prepared which contained 250 mg activity azithromycin. The formula for these capsules is presented in Table I. The dissolution behavior of these capsules was evaluated by the method previously discussed, using rotating paddles, 100 rpm, 900 ml pH 6.0 phosphate buffer at 37 degrees C. The average % azithromycin dissolved at 15 minutes was 25%, and at 30 minutes was 76%.

The effect of feeding on azithromycin bioavailability was determined as follows. Eleven healthy male human volunteers were orally dosed with 500 mg azithromycin (2×250 mg capsules), on each of 2 occasions. On one occasion, the subjects were dosed after an overnight fast (food and fluid) of 12 hr. The dose was swallowed with 150 ml water, and a further 150 ml water was taken at 1 hr post-dosing. On the other occasion, the subjects consumed a meal consisting of milk, bread and butter, bacon, 2 fried eggs, and coffee. The dose was administered with 150 ml water within 30 minutes of completion of the meal. Blood samples were withdrawn prior to dosing, and at 0.5, 1, 2, 3, 4, 6, 8, 12, and 24 hr post-dosing. Serum azithromycin concentration was determined using a high performance liquid chromatography assay. For each subject under each dosing condition, the area under the drug serum concentration vs. time curve (AUC) was determined for each feeding condition. The ratio AUCfed/AUCfasted was used as a measure of the effect of food on oral bioavailability. The average AUCfed/AUCfasted was 0.22, with lower and upper 90% confidence levels of 0.06 and 0.84, respectively.

TABLE I

Formulation of 250 mg Azithromycin Capsules. Prepared in #0 white opaque locking type capsules.

| INGREDIENT | MG/CAPSULE |
| --- | --- |
| Azithromycin* | 263.72 |
| Lactose, anhydrous | 149.88 |
| Corn starch, hydrous | 47.0 |
| Magnesium stearate/Sodium lauryl sulfate (90/10) | 9.40 |
| TOTAL | 470.0 |

*Based on a bulk potency of 94.8%; Non-stoichiometric hydrate.

EXAMPLE 2

This example is comparative and demonstrates the effect of a high fat breakfast on systemic exposure of azithromycin dosed in a capsule dosage form which dissolved more quickly than the capsules of Example 1.

Azithromycin capsules (250 mg strength) were prepared according to the formula in Table II. Dissolution of azithromycin from these capsules was evaluated as in Example 1. In 15 minutes, 97% of the encapsulated azithromycin was dissolved.

The effect of feeding on azithromycin bioavailability from this dosage form was determined as follows. Twelve healthy male human volunteers were orally dosed with 500 mg azithromycin (2×250 mg capsules), on each of 2 occasions. On one occasion, the subjects were dosed after an overnight fast, and on the other occasion the subjects were dosed after consumption of a meal consisting of two eggs fried in one tablespoon butter, two strips of bacon, two ounces of ham, two pieces of toast with two teaspoons of butter and two pats of jelly, and eight ounces whole-fat milk. The oral doses were administered with 250 ml water. Blood samples were withdrawn prior to dosing, and at 0.5, 1, 2, 3, 4, 6, 8, 12, 18, 24, 48, 72, and 96 hr post-dosing. Serum azithromycin concentration was determined using a high performance liquid chromatography assay. For each subject under each dosing condition, the area under the drug serum concentration vs. time curve (AUC) was determined for each feeding condition.

The ratio AUCfed/AUCfasted was used as a measure of the effect of food on azithromycin oral bioavailability. The average AUCfed/AUCfasted was 0.80, with lower and upper 90% confidence levels of 0.67 and 0.96, respectively.

TABLE II

Formula for Azithromycin capsules. This formula was prepared as a dry granulation and was loaded into #0 opaque locking capsules.

| INGREDIENT | MG/CAPSULE |
| --- | --- |
| Azithromycin Dihydrate* | 262.05 |
| Lactose, anhydrous | 151.55 |
| Corn starch, hydrous | 47.00 |
| Magnesium stearate/Sodium lauryl sulfate | 9.40 |
| TOTAL | 470.00 |

*Equivalent to 250 mg azithromycin, based on a bulk potency of 95.4%.

EXAMPLE 3

This example is comparative and demonstrates the effect of a light breakfast on systemic exposure of azithromycin dosed in a capsule dosage form which dissolves quickly.

Azithromycin capsules (250 mg strength) were prepared according to the formula in Table II. Dissolution of azithromycin from these capsules was evaluated as in Example 1. In 15 minutes, 99% of the encapsulated azithromycin was dissolved.

The effect of a light (Continental) breakfast on azithromycin bioavailability from this dosage form was determined as follows. Twelve healthy male human volunteers were orally dosed with 1000 mg azithromycin (4×250 mg capsules), on each of 2 occasions. On one occasion, the subjects were dosed after a 12 hr fast, and on the other occasion the subjects were dosed after consumption of a light breakfast consisting of two rolls with butter and jam and Ca. 300 ml of coffee or tea with milk. The oral doses were administered with 240 ml water. Blood samples were withdrawn prior to dosing, and at 0.5, 1, 1.5, 2, 2.5, 3, 3.5, 4, 5, 6, 8, 12, 24, and 46.5 hr post-dosing. Serum azithromycin concentration was determined using a high performance liquid chromatography assay. For each subject under each dosing condition, the area under the drug serum concentration vs. time curve (AUC) was determined for each feeding condition.

The ratio AUCfed/AUCfasted was used as a measure of the effect of food on oral bioavailability. The average AUCfed/AUCfasted was 0.71, with lower and upper 90% confidence levels of 0.53 and 0.95, respectively.

EXAMPLE 4

This example demonstrates the effect of a high fat breakfast on systemic exposure of azithromycin dosed in a tablet dosage form which dissolves quickly.

Azithromycin tablets were prepared according to the formula given in Table III. Dissolution evaluation was carried out as in Example 1. At 30 minutes, 100% of the azithromycin was dissolved.

The effect of feeding on azithromycin bioavailability from these tablets was determined as follows. Twelve healthy male human volunteers were orally dosed with 500 mg azithromycin (2×250 mg tablets), on each of 2 occasions. On one occasion, the subjects were dosed after an overnight fast, and on the other occasion the subjects were dosed after consumption of a meal consisting of two eggs fried in one tablespoon butter, two strips of bacon, two pieces of toast with two teaspoons of butter and two pats of jelly, eight ounces whole-fat milk, and 6 ounces hash-brown potatoes, ingested over a twenty minute period. The oral doses were administered with 240 ml water. Blood samples were withdrawn prior to dosing, and at 0.5, 1, 2, 3, 4, 6, 8, 12, 18, 24, 48, 72, and 96 hr post-dosing. Serum azithromycin concentration was determined using a high performance liquid chromatography assay. For each subject under each dosing condition, the area under the drug serum concentration vs. time curve (AUC) was determined for each feeding condition.

The ratio AUCfed/AUCfasted was used as a measure of the effect of food on oral bioavailability. The average AUCfed/AUCfasted was 0.97, with lower and upper 90% confidence levels of 0.82 and 1.13, respectively.

TABLE III

Formula for azithromycin film coated tablets. This formula was compressed to form a 0.262" × 0.5312" modified capsular, upper engraved "Pfizer", lower scored, tablet, and was coated with "pink Opadry".

| INGREDIENT | WEIGHT (MG/UNIT) |
| --- | --- |
| Azithromycin dihydrate* | 262.05 |
| Pregelatinized starch** | 27.00 |
| Calcium phosphate dibasic, anhydrous | 138.84 |
| Sodium croscarmellose*** | 9.00 |
| Magnesium stearate/Sodium lauryl sulfate (90/10) | 13.11 |
| Pink Opadry II## | 18.00 |

*Equivalent to 250 mg azithromycin, based on a bulk potency of 95.4%.
**Starch 1500.
***Ac-Di-Sol.
Contains lactose, hydroxypropyl methylcellulose, titanium dioxide, triacetin, and D&C Red No. 30 Aluminum Lake.

EXAMPLE 5

This example demonstrates the effect of a Japanese meal on systemic exposure of azithromycin dosed in a tablet dosage form which dissolves quickly.

A tablet dosage form of azithromycin was prepared according to the formula described in Table IV. Dissolution of this dosage form was evaluated as in Example 1. In 15 minutes, 100% of the azithromycin dose was dissolved.

The effect of feeding on azithromycin bioavailability from these tablets was determined as follows. Eight healthy male human volunteers were orally dosed with 500 mg azithromycin (2×250 mg tablets), on each of 2 occasions. On one occasion, the subjects were dosed after a 12 hr fast, and on the other occasion the subjects were dosed 30 minutes after consumption of a Japanese meal consisting of rice, miso soup, fried egg, seaweed, spinach, and pickles. The oral doses were administered with 200 ml water. Blood samples were withdrawn prior to dosing, and at 0.5, 1, 2, 3, 4, 6, 9, 12, 24, 48, 72, 96, 120, 144, and 168 hr post-dosing. Serum azithromycin concentration was determined using a high performance liquid chromatography assay. For each subject under each dosing condition, the area under the drug serum concentration vs. time curve (AUC) was determined for each feeding condition.

The ratio AUCfed/AUCfasted was used as a measure of the effect of food on oral bioavailability. The average AUCfed/AUCfasted was 1.00, with lower and upper 90% confidence levels of 0.87 and 1.15, respectively.

TABLE IV

Azithromycin film-coated tablet formula. Capsular plain white film-coated tablets (0.262" × 0.5312") were compressed and then coated with "White Opadry"and "Clear Opadry".

| INGREDIENT | WEIGHT (MG/TABLET) |
| --- | --- |
| Azithromycin dihydrate* | 262.05 |
| Pregelatinized starch** | 27.00 |
| Calcium phosphate dibasic, Anhydrous | 138.84 |
| Sodium croscarmellose*** | 9.00 |
| White Opadry## | 12.825 |
| Clear Opadry### | 0.675 |
| Magnesium Stearate/ Sodium Lauryl Sulfate (90/10) | 13.11 |

*Equivalent to 250 mg azithromycin, based on a bulk potency of 95.4%.
**Starch 1500.
***Ac-Di-Sol.
Contains hydroxypropyl methylcellulose, titanium dioxide, polyethyleneglycol, and polysorbate 80.
Contains hydroxypropyl methylcellulose and polyethyleneglycol.

EXAMPLE 6

This example compares the effects of a high fat breakfast and a low fat breakfast on systemic exposure of azithromycin dosed in a "Powder for Oral Suspension" dosage form.

An azithromycin "Powder for Oral Suspension" was prepared according to the formula in Table V. This formula was designed to wet and disperse quickly when reconstituted with an aqueous vehicle. Dissolution of this suspension was evaluated as described in the "Detailed Description". In 15 minutes 97% of the azithromycin dose dissolved; in 30 minutes 99.6% of the azithromycin dose dissolved.

The effect of a high fat meal and a low fat meal on azithromycin bioavailability from this suspension dosage form was determined as follows. Six healthy male human volunteers were orally dosed with 500 mg azithromycin (12.5 ml of a 40 mg/ml oral suspension), on each of 3 occasions. On one occasion, the subjects were dosed after an overnight fast of 10–12 hr. On another occasion the subjects were dosed after consumption of a high fat meal consisting of two eggs fried in one tablespoon butter, two strips of bacon, two pieces of toast with two pats of butter, eight ounces whole-fat milk, and 6 ounces hash-brown potatoes, ingested over a twenty minute period. On the third occasion, the subjects were dosed after consumption of a low fat meal consisting of one ounce of Cheerios (registered trademark of General Mills Inc.) cereal and eight ounces of whole milk. The oral doses were administered with 240 ml water (two 60 ml rinses of the oral syringe plus an additional 120 ml). Blood samples were withdrawn prior to dosing, and at 0.5, 1, 2, 3, 4, 6, 8, 12, 18, 24, 48, 72, and 96 hr post-dosing. Serum azithromycin concentration was determined using a high performance liquid chromatography assay. For each subject under each dosing condition, the area under the drug serum concentration vs. time curve (AUC) was determined for each feeding condition.

The ratio AUCfed/AUCfasted was used as a measure of the effect of food on oral bioavailability. For the high fat meal, the average AUCfed/AUCfasted was 1.01, with lower and upper 90% confidence levels of 0.79 and 1.28, respectively. For the low fat meal, the average AUCfed/AUCfasted was 1.04, with lower and upper 90% confidence levels of 0.82 and 1.33, respectively.

TABLE V

Formula for azithromycin "Powder for Oral Suspension". To reconstitute this formulation, 0.52 ml water was added per gm dry formulation.

| INGREDIENT | WEIGHT (MG/BOTTLE) |
| --- | --- |
| Azithromycin dihydrate* | 838.57 |
| Sucrose | 15487.74 |
| Sodium phosphate tribasic, anhydrous | 70.01 |
| Hydroxypropylcellulose (Klucel-EF) | 26.62 |
| Xanthan gum (Keltrol) | 26.62 |
| FD&C Red #40 | 0.67 |
| Spray Dried Cherry #11929 | 59.94 |
| Art. Creme de Vanilla #11489 | 133.28 |
| S.D. Art. Banana #15223 | 99.96 |
| TOTAL | 16743.41 |

*Based on a bulk potency of 95.4%.

EXAMPLE 7

This example demonstrates the effect of a high fat breakfast on systemic exposure of azithromycin dosed in a "Single Dose Packet" (sachet) dosage form.

A "Single Dose Packet" (sachet) dosage form of azithromycin was prepared according to the formula described in Table VI. Dissolution of this dosage form was evaluated as described in the "Detailed Description" above. In 15 minutes, 99% of the azithromycin was dissolved.

The effect of feeding on azithromycin bioavailability from this sachet dosage form was determined as follows. Twelve healthy male human volunteers were orally dosed with 1000 mg azithromycin (1 gm sachet), on each of 2 occasions. On one occasion, the subjects were dosed after an overnight fast of at least 12 hr, and on the other occasion the subjects were dosed after consumption of a high-fat meal consisting of two eggs fried in one tablespoon butter, two strips of bacon, two pieces of toast with two teaspoons of butter and with two pats of jelly, eight ounces whole-fat milk, and 6 ounces hash-brown potatoes. The oral doses were administered with 240 ml water (two 60 ml rinses of the oral syringe plus an additional 120 ml). Blood samples were withdrawn prior to dosing, and at 0.25, 0.5, 1, 1.5, 2, 2.5, 3, 4, 6, 8, 12, 18, 24, 48, 72, 96, and 120 hr post-dosing. Serum azithromycin concentration was determined using a high performance liquid chromatography assay. For each subject under each dosing condition, the area under the drug serum concentration vs. time curve (AUC) was determined for each feeding condition.

The ratio AUCfed/AUCfasted was used as a measure of the effect of food on oral bioavailability. The average AUCfed/AUCfasted was 1.12, with lower and upper 90% confidence levels of 0.99 and 1.27.

TABLE VI

Formula for azithromycin "Unit Dose Packet" dosage form. This blend was prepared, and filled into 3.25" × 4" white paper/aluminum/polyethylene laminate sachets. To reconstitute for dosing, the contents of a sachet is added to 60 ml water, and stirred well.

| INGREDIENT | WEIGHT (GM/UNIT) |
| --- | --- |
| Azithromycin dihydrate* | 1.048 |
| Sucrose | 9.707 |
| Sodium phosphate tribasic, anhydrous | 0.088 |
| Colloidal silicon dioxide | 0.055 |
| Spray Dried art. cherry #11929 | 0.038 |
| Spray Dried art. banana #15223 | 0.064 |
| TOTAL | 11.000 |

*Equivalent to 1 gm azithromycin, based on a bulk potency of 95.4% for azithromycin dihydrate.

EXAMPLE 8

Azithromycin tablets of this invention were prepared at 150, 200, 250, 300, 500, and 600 mg dosage strengths. Tablet cores were prepared by wet granulation of all tablet core ingredients (except magnesium stearate/sodium lauryl sulfate). The dried granules were blended with the lubricant mixture magnesium stearate/sodium lauryl sulfate, followed by tableting on a tablet press. Tablets were coated with an aqueous film coat comprising colored and/or clear Opadry. These tablet formulations do not exhibit an adverse food effect. Tablet formulations were as described in Table VII.

TABLE VII

Examples of azithromycin tablet formulations which do not exhibit a food effect.

| Component | WEIGHT (MG/TABLET) | | | | | |
| --- | --- | --- | --- | --- | --- | --- |
| | 150 MG STRENGTH | 200 MG STRENGTH | 250 MG STRENGTH | 300 MG STRENGTH | 500 MG STRENGTH | 600 MG STRENGTH |
| Azithromycin dihydrate* | 157.23 | 209.613 | 262.05 | 314.46 | 524.10 | 628.93 |
| Pregelatinized starch** | 16.20 | 21.60 | 27.00 | 32.40 | 54.00 | 64.80 |
| Calcium phosphate dibasic, anhydrous | 83.305 | 111.01 | 138.84 | 166.61 | 277.68 | 333.21 |
| Sodium croscarmellose# | 5.400 | 7.200 | 9.00 | 10.80 | 18.00 | 21.60 |

TABLE VII-continued

Examples of azithromycin tablet formulations which do not exhibit a food effect.

| Component | WEIGHT (MG/TABLET) | | | | | |
|---|---|---|---|---|---|---|
| | 150 MG STRENGTH | 200 MG STRENGTH | 250 MG STRENGTH | 300 MG STRENGTH | 500 MG STRENGTH | 600 MG STRENGTH |
| Magnesium stearate/ Sodium lauryl sulfate (90/10) | 7.865 | 10.486 | 13.11 | 15.73 | 26.22 | 31.46 |
| Opadry@ | 8.1 | 10.8 | 13.5 | 16.2 | 27.0 | 32.4 |
| TOTAL | 278.1 | 370.8 | 463.5 | 556.2 | 927.0 | 1,112.4 |

*Based on a theoretical potency of 95.4%.
**Starch 1500.
e.g. Ac-Di-Sol.
@Hydroxypropylmethylcellulose and appropriate plasticizers, film-coating adjuvants, opacifier, and lakes.

EXAMPLE 9

Additional tablet formulations of azithromycin (250 mg) are prepared which do not exhibit an adverse food effect and are described in Table VIII. The diluent in these formulations (calcium phosphate dibasic, anhydrous) may be substituted by calcium phosphate dibasic dihydrate, microcrystalline cellulose, lactose NF/BP/EP/JP, or other appropriate diluent. The lubricant in these tablets (magnesium stearate/ sodium lauryl sulfate, 90/10) may be substituted by magnesium stearate and/or colloidal silica or sodium stearyl fumarate. Magnesium stearate and sodium stearyl fumarate are generally used in amounts constituting 0.5–7% of the total tablet weight. Colloidal silica is generally used in an amount constituting 0.1–1% of the total tablet weight. While considerable latitude in relative excipient ratios is possible, the calcium phosphate/pregelatinized starch ratio should be around 2:1 or greater. The Opadry film coat is not necessary to achieve food-independent drug exposure, but serves to improve ease-of-swallowing and tablet appearance and serves to differentiate strengths. The Opadry coat may comprise between 2–6% of the total tablet weight. Tablets at other potencies may be obtained by maintaining the approximate azithromycin/excipient ratios described in Table VIII, and increasing or decreasing total tablet weight.

EXAMPLE 10

Further 250 mg azithromycin tablet formulations are prepared which do not exhibit an adverse food effect and are presented in Tables IX and X. In these formulations, maize starch, sodium starch glycolate, and crosslinked polyvinylpyrrolidone serve as disintegrants. Calcium phosphate dibasic, lactose NF/BP/EP, and microcrystalline cellulose serve as diluents.

Magnesium stearate/sodium lauryl sulfate serves as a lubricant. Magnesium stearate/sodium lauryl sulfate may be substituted by magnesium stearate and/or colloidal silica or sodium stearyl fumarate. Magnesium stearate and sodium stearyl fumarate are generally used in amounts constituting 0.5–7% of the total tablet weight. Colloidal silica is generally used in an amount constituting 0.1–1% of the total tablet weight. While considerable latitude in relative excipient ratios is possible, the diluent/disintegrant ratio should be around 2:1 or greater. The Opadry film coat is not necessary to achieve food-independent drug exposure, but serves to improve ease-of-swallowing and tablet appearance. The Opadry coat may comprise between 2–6% of the total tablet weight. Tablets at other potencies are obtained by maintaining the approximate azithromycin/excipient ratios described in Tables IX and X, and increasing or decreasing total tablet weight. These formulas are illustrative, and substitutions of other disintegrants, diluents, and lubricants are possible, as known in the art.

TABLE VIII

Examples of azithromycin tablet formulations (250 mg) which do not exhibit an adverse food effect.

| COMPONENT | WEIGHT (MG/TABLET) | | |
|---|---|---|---|
| | FORMULATION 1 | FORMULATION 2 | FORMULATION 3 |
| Azithromycin dihydrate | 262.05 | 262.05 | 262.05 |
| Pregelatinized starch | 50.0 | 13.9 | 50.0 |
| Calcium phosphate dibasic, anh. | 115.84 | 140.94 | 104.84 |
| Sodium croscarmellose | 9.0 | 20.0 | 20.0 |
| Magnesium stearate/sodium lauryl sulfate | 13.11 | 13.11 | 13.11 |
| Opadry@ | 13.50 | 13.50 | 13.50 |
| TOTAL | 463.5 | 463.5 | 463.5 |

@Hydroxypropylmethylcellulose and appropriate plasticizers, film-coating adjuvants, opacifiers, and lakes.

TABLE IX azithromycin tablet formulations which do not exhibit an adverse food effect.

| COMPONENT | WEIGHT (MG/TABLET) | | |
|---|---|---|---|
| | FORMULATION 4 | FORMULATION 5 | FORMULATION 6 |
| Azithromycin dihydrate† | 262.05 | 262.05 | 262.05 |
| Maize starch* | 13.9 | 27.0 | 50.0 |
| Calcium phosphate, dibasic** OR Lactose NF/BP/EP/JP OR Microcrystalline cellulose | 151.94 | 138.84 | 115.84 |
| Sodium starch glycolate# OR Crosslinked polyvinylpyrrolidone## | 9.0 | 9.0 | 9.0 |

TABLE IX-continued azithromycin tablet formulations which do not exhibit an adverse food effect.

| COMPONENT | WEIGHT (MG/TABLET) | | |
|---|---|---|---|
| | FORMU-LATION 4 | FORMU-LATION 5 | FORMU-LATION 6 |
| Magnesium stearate/sodium lauryl sulfate | 13.11 | 13.11 | 13.11 |
| Opadry@ | 13.5 | 13.5 | 13.5 |
| TOTAL | 463.5 | 463.5 | 463.5 |

†Equivalent to 250 mg azithromycin.
*Also called starch NF or cornstarch
**Either anhydrous or dihydrate
e.g. Explotab or Primojel
e.g. PVP-XL from International Specialty Products Inc.
@Hydroxypropylmethylcellulose and appropriate plasticizers, film-coating adjuvants, opacifiers, and lakes.

TABLE X

Examples of azithromycin tablet formulations which do not exhibit an adverse food effect.

| COMPONENT | WEIGHT (MG/TABLET) | | |
|---|---|---|---|
| | FORMU-LATION 7 | FORMU-LATION 8 | FORMU-LATION 9 |
| Azithromycin dihydrate† | 262.05 | 262.05 | 262.05 |
| Maize starch* | 13.9 | 27.0 | 27.0 |
| Calcium phosphate, dibasic** OR Lactose NF/BP/EP/JP OR Microcrystalline cellulose | 140.94 | 144.84 | 127.84 |
| Sodium starch glycolate# OR Crosslinked polyvinylpyrrolidone## | 20.0 | 3.0 | 20.0 |
| Magnesium stearate/sodium lauryl sulfate | 13.11 | 13.11 | 13.11 |
| Opadry@ | 13.5 | 13.5 | 13.5 |
| TOTAL | 463.5 | 463.5 | 463.5 |

*Also called starch NF or cornstarch
**Either anhydrous or dihydrate
e.g. Explotab or Primojel
e.g. PVP-XL from International Specialty Products Inc.
@Hydroxypropylmethylcellulose and appropriate plasticizers, film-coating adjuvants, opacifiers, and lakes.
†Equivalent to 250 mg azithromycin.

EXAMPLE 11

The "Powder for Oral Suspension" formulation described in Table XI was prepared. This formulation does not exhibit an adverse food effect.

TABLE XI

A formulation for azithromycin "Powder for Oral Suspension"

| COMPONENT | WEIGHT (MG/GM) |
|---|---|
| Azithromycin dihydrate | 47.97 |
| Sucrose NF | 579.71 |
| Sorbitol, crystalline, powder, NF/FCC | 289.86 |
| Sodium carbonate, anhydrous, NF | 18.84 |
| Sodium benzoate, NF/FCC | 4.35 |
| Tragacanth gum powder, NF | 14.49 |
| Titanium dioxide USP | 14.49 |
| Colloidal silicon dioxide, NF | 1.45 |
| Aminoacetic acid (glycine) USP | 5.80 |
| Spray-dried Art. Strawberry #22653 | 15.26 |
| Tropical apple punch #26508 | 7.63 |
| Spray-dried peppermint stick #15634 | 0.15 |
| TOTAL | 1000.00 |

EXAMPLE 12

Azithromycin "Powder for Oral Suspension" formulations are prepared as illustrated in Tables XII and XIII. The unit potency of these formulations is 600 mg azithromycin/bottle, and the use potency after constitution with water is 40 mg/ml. To constitute, 0.52 ml water is added per gm of blend. 9 mL water and 16.74 gm blend produce approximately 20 ml suspension. These formulations include 200 mg Azithromycin/bottle overfill. The listed "flavor system" may be freely substituted with other flavors which provide a pleasant taste and are stable at pH 10 over the shelf-life of the constituted suspension (approximately 5 days). The dye may also be freely substituted. The formulations in this Example are illustrative, and not limiting. These formulations do not exhibit an adverse food effect.

TABLE XII

Examples of formulations of Azithromycin "Powder for Oral Suspension"

| COMPONENT | WEIGHT (MG/BOTTLE) | | |
|---|---|---|---|
| | FORMU-LATION 1 | FORMU-LATION 2 | FORMU-LATION 3 |
| Azithromycin dihydrate | 838.57 | 838.57 | 838.57 |
| Sucrose NF | 15487.74 | 15370.54 | 15487.74 |
| Sodium phosphate tribasic anhydrous | 70.01 | 70.01 | 70.01 |
| Hydroxypropyl-cellulose | 26.62 | 26.62 | 0 |
| Xanthan gum | 26.62 | 26.62 | 0 |
| Sodium carboxy-methylcellulose | 0 | 0 | 53.24 |
| Colloidal silicon dioxide | 0 | 16.74 | 0 |
| Glycine | 0 | 100.46 | 0 |
| Spray-dried cherry #11929 | 59.94 | 59.94 | 59.94 |
| Art. Creme de Vanilla #11489 | 133.28 | 133.28 | 133.28 |
| Spray-dried Art. Banana #15223 | 99.96 | 99.96 | 99.96 |
| FD&C Red #40 | 0.67 | 0.67 | 0.67 |
| TOTAL | 16743.41 | 16743.41 | 16743.41 |

TABLE XIII

Examples of formulations of Azithromycin "Powder for Oral Suspension"

| COMPONENT | WEIGHT (MG/BOTTLE) | | |
|---|---|---|---|
| | FORMU-LATION 4 | FORMU-LATION 5 | FORMU-LATION 6 |
| Azithromycin dihydrate | 838.57 | 838.57 | 838.57 |
| Sorbitol | 15138.55 | 7743.87 | 7656.37 |
| Sucrose NF | 0 | 7743.87 | 7656.37 |
| Sodium carbonate, anhydrous, NF | 302.00 | 0 | 150.00 |
| Sodium phosphate tribasic anhydrous | 0 | 70.01 | 35.00 |
| Hydroxypropyl-cellulose | 0 | 26.62 | 17.75 |
| Xanthan gum | 0 | 26.62 | 17.75 |
| Sodium carboxy-methylcellulose | 53.24 | 0 | 17.75 |
| Colloidal silicon dioxide | 16.74 | 0 | 10.00 |
| Glycine | 100.46 | 0 | 50.00 |
| Spray-dried cherry #11929 | 59.94 | 59.94 | 59.94 |
| Art. Creme de Vanilla #11489 | 133.28 | 133.28 | 133.28 |
| Spray-dried Art. Banana #15223 | 99.96 | 99.96 | 99.96 |
| FD&C Red #40 | 0.67 | 0.67 | 0.67 |
| TOTAL | 16743.41 | 16743.41 | 16743.41 |

EXAMPLE 14

The following formulations of unit dose packets of azithromycin are prepared as being exemplary, not limiting, of the invention (Tables XIV and XV). The flavor system for these dosage forms may be freely substituted with any flavor system which provides a pleasant taste when the contents of the packet are reconstituted in water or an aqueous beverage. When constituted in water or an aqueous beverage, these dosage forms do not exhibit an adverse food effect.

TABLE XIV

Examples of unit dose packet formulations.

| COMPOSITION | FORMU-LATION 1 | FORMU-LATION 2 | FORMU-LATION 3 |
|---|---|---|---|
| Azithromycin dihydrate | 1.048 | 1.048 | 1.048 |
| sucrose | 9.707 | 9.707 | 5.0 |
| sorbitol | 0 | 0 | 0 |
| sodium phosphate tribasic, anhydrous | 0.04 | 0.2 | 0.088 |
| sodium carbonate, anhydrous | 0 | 0 | 0 |
| glycine | 0 | 0 | 0 |
| colloidal silicon dioxide | 0.022 | 0.22 | 0.055 |
| Spray-dried art. cherry #11929 | 0.038 | 0.038 | 0.038 |
| Spray-dried art. banana #15223 | 0.064 | 0.064 | 0.064 |

TABLE XV

Examples of unit dose packet formulations.

| COMPOSITION | FORMU-LATION 1 | FORMU-LATION 2 | FORMU-LATION 3 |
|---|---|---|---|
| Azithromycin dihydrate | 1.048 | 1.048 | 1.048 |
| sucrose | 0 | 4.85 | 4.85 |
| sorbitol | 9.707 | 4.85 | 4.85 |
| sodium phosphate tribasic, anhydrous | 0.088 | 0.088 | 0.044 |
| sodium carbonate, anhydrous | 0 | 0 | 0.022 |
| glycine | 0 | 0 | 0.022 |
| colloidal silicon dioxide | 0.055 | 0.055 | 0.055 |
| Spray-dried art. cherry #11929 | 0.038 | 0.038 | 0.038 |
| Spray-dried art. banana #15223 | 0.064 | 0.064 | 0.064 |

What is claimed is:

1. An oral dosage form of azithromycin which is in the form of a tablet made by wet granulation, which is administrable to a mammal that has eaten, which comprises azithromycin and a disintegrant, and which exhibits no adverse food effect, said dosage form effecting at least about 90% dissolution of azithromycin within about 30 minutes when an amount of the dosage form equivalent to 200 mg of azithromycin is tested as set forth in USP test <711> in a USP-2 dissolution apparatus under conditions at least as stringent as the following: 900 ml sodium phosphate buffer pH 6.0, 37° C., with paddles turning at 100 rpm, provided that said dosage form contains less than a taste-masking amount of an alkaline earth metal oxide or hydroxide.

2. A dosage form as defined in claim 1, wherein said mammal is a human.

3. A dosage form as defined in claim 1, further comprising a flavoring agent.

4. An oral dosage form of azithromycin which is in the form of a powder for oral suspension containing anhydrous buffer, which is administrable to a mammal that has eaten, which comprises azithromycin, one or more thickening agents, and said anhydrous buffer, and which exhibits no adverse food effect, said dosage form effecting at least about 90% dissolution of azithromycin within about 30 minutes when an amount of the dosage form equivalent to 200 mg of azithromycin is tested as set forth in USP test <711> in a USP-2 dissolution apparatus under conditions at least as stringent as the following: 900 ml sodium phosphate buffer, pH 6.0, 37° C., with paddles turning at 100 rpm, provided that said dosage form contains less than a taste-masking amount of an alkaline earth metal oxide or hydroxide.

5. A dosage form as defined in claim 4, wherein said mammal is a human.

6. A dosage form as defined in claim 4, further comprising a flavoring agent.

7. A dosage form as defined in claim 6, wherein said flavoring agent is a flavor system consisting of cherry, vanilla, and banana.

8. A dosage form as defined in claim 4, in the form of a suspension made from said powder.

9. An oral dosage form of azithromycin which is in the form of a unit dose packet containing a dispersing agent, which is administrable to a mammal that has eaten, which comprises azithromycin and said dispersing agent, and which exhibits no adverse food effect, said dosage form effecting at least about 90% dissolution of azithromycin within about 30 minutes when an amount of the dosage form equivalent to 200 mg of azithromycin is tested as set forth in USP test <711> in a USP-2 dissolution apparatus under conditions at least as stringent as the following: 900 ml sodium phosphate buffer, pH 6.0, 37° C., with paddles turning at 100 rpm, provided that said dosage form contains less than a taste-masking amount of an alkaline earth metal oxide or hydroxide.

10. A dosage form as defined in claim 9, wherein said mammal is a human.

11. A dosage form as defined in claim 9, further comprising an anhydrous buffer.

12. A dosage form as defined in claim 9, wherein said dispersing agent is colloidal silicon dioxide.

13. A dosage form as defined in claim 9, in the form of a suspension made from said unit dose packet.

14. An oral dosage form of azithromycin which is in the form of a tablet made by wet granulation, which is administrable to a mammal that has eaten, which comprises azithromycin and a disintegrant, and which exhibits no adverse food effect, said dosage form exhibiting a value of $(AUC_{fed})/(AUC_{fst})$ of at least 0.80 with a lower 90% confidence limit of at least 0.75, provided that said dosage form contains less than a taste-masking amount of an alkaline earth metal oxide or hydroxide.

15. A dosage form as defined in claim 14, wherein said mammal is a human.

16. A dosage form as defined in claim 14, further comprising a flavoring agent.

17. An oral dosage form of azithromycin which is in the form of a powder for oral suspension containing an anhydrous buffer, which is administrable to a mammal that has eaten, which comprises azithromycin, one or more thickening agents, and said anhydrous buffer, and which exhibits no adverse food effect, said dosage form exhibiting a value of $(AUC_{fed})/(AUC_{fst})$ of at least 0.80 with a lower 90% confidence limit of at least 0.75, provided that said dosage form contains less than a taste-masking amount of an alkaline earth metal oxide or hydroxide.

18. A dosage form as defined in claim 17, wherein said mammal is a human.

19. A dosage form as defined in claim 17, further comprising a flavoring agent.

20. A dosage form as defined in claim 19, wherein said flavoring agent is a flavoring system consisting of cherry, vanilla, and banana.

21. A dosage form as defined in claim 17, in the form of a suspension made from said powder.

22. An oral dosage form of azithromycin which is in the form of a unit dose packet containing a dispersing agent, which is administrable to a mammal that has eaten, which comprises azithromycin and said dispersing agent, and which exhibits no adverse food effect, said dosage form exhibiting a value of $(AUC_{fed})/(AUC_{fst})$ of at least 0.80 with a lower 90% confidence limit of at least 0.75, provided that said dosage form contains less than a taste-masking amount of an alkaline earth metal oxide or hydroxide.

23. A dosage form as defined in claim 22, wherein said mammal is a human.

24. A dosage form as defined in claim 22, further comprising an anhydrous buffer.

25. A dosage form as defined in claim 22, wherein said dispersing agent is colloidal silicon dioxide.

26. A dosage form as defined in claim 22, in the form of a suspension made from said unit dose packet.

27. A dosage form as defined in claim 1, comprising:
58.2% azithromycin dihydrate;
6.0% pregelatinized starch;
30.9% anhydrous dibasic calcium phosphate;
2.0% sodium croscarmellose; and
2.9% lubricant.

28. A dosage form as defined in claim 1, comprising:
58.2% azithromycin dihydrate;
11.1% pregelatinized starch;
25.7% anhydrous dibasic calcium phosphate;
2.0% sodium croscarmellose; and
2.9% lubricant.

29. A dosage form as defined in claim 1, comprising:
58.2% azithromycin dihydrate;
3.1% pregelatinized starch;
31.3% anhydrous dibasic calcium phosphate;
4.4% sodium croscarmellose; and
2.9% lubricant.

30. A dosage form as defined in claim 1, comprising:
58.2% azithromycin dihydrate;
11.1% pregelatinized starch;
23.3% anhydrous dibasic calcium phosphate;
4.4% sodium croscarmellose; and
2.9% lubricant.

31. A dosage form as defined in claim 1, comprising:
58.2% azithromycin dihydrate;
3.1% maize starch;
33.8% dibasic calcium phosphate, lactose, or microcrystalline cellulose;
2.0% sodium starch glycolate or crosslinked polyvinylpyrrolidone; and
2.9% lubricant.

32. A dosage form as defined in claim 1, comprising:
58.2% azithromycin dihydrate;
6.0% maize starch;
30.9% dibasic calcium phosphate, lactose, or microcrystalline cellulose;
2.0% sodium starch glycolate or crosslinked polyvinylpyrrolidone; and
2.9% lubricant.

33. A dosage form as defined in claim 1, comprising:
58.2% azithromycin dihydrate;
11.1% maize starch;
25.7% dibasic calcium phosphate, lactose, or microcrystalline cellulose;
2.0% sodium starch glycolate or crosslinked polyvinylpyrrolidone; and
2.9% lubricant.

34. A dosage form as defined in claim 1, comprising:
58.2% azithromycin dihydrate;
3.1% maize starch;
31.3% dibasic calcium phosphate, lactose, or microcrystalline cellulose;
4.4% sodium starch glycolate or crosslinked polyvinylpyrrolidone; and
2.9% lubricant.

35. A dosage form as defined in claim 1, comprising:
58.2% azithromycin dihydrate;
6.0% maize starch;

32.2% dibasic calcium phosphate, lactose, or microcrystalline cellulose;
0.7% sodium starch glycolate or crosslinked polyvinylpyrrolidone; and
2.9% lubricant.
36. A dosage form as defined in claim 1, comprising:
58.2% azithromycin dihydrate;
6.0% maize starch;
28.4% dibasic calcium phosphate, lactose, or microcrystalline cellulose;
4.4% sodium starch glycolate or crosslinked polyvinylpyrrolidone; and
2.9% lubricant.
37. A dosage form as defined in claim 4, comprising:
5.0% azithromycin dihydrate;
92.5% sucrose;
0.4% anhydrous tribasic sodium phosphate;
0.2% hydroxypropylcellulose;
0.2% xanthan gum;
trace coloring; and
1.8% flavoring.
38. A dosage form as defined in claim 4, comprising:
4.8% azithromycin dihydrate;
58.0% sucrose;
29.0% sorbitol;
1.9% anhydrous sodium carbonate;
0.4% sodium benzoate;
1.5% tragacanth gum powder;
1.5% titanium dioxide;
1.15% colloidal silicon dioxide;
0.6% glycine; and
2.3% flavoring.
39. A dosage form as defined in claim 4, comprising:
5.0% azithromycin dihydrate;
91.8% sucrose;
0.4% anhydrous tribasic sodium phosphate;
0.2% hydroxypropylcellulose;
0.2% xanthan gum;
0.1% colloidal silicon dioxide;
0.6% glycine;
trace coloring; and
1.8% flavoring.
40. A dosage form as defined in claim 4, comprising:
5.0% azithromycin dihydrate;
92.5% sucrose;
0.4% anhydrous tribasic sodium phosphate;
0.3% sodium carboxymethylcellulose;
trace coloring; and
1.8% flavoring.
41. A dosage form as defined in claim 4, comprising:
5.0% azithromycin dihydrate;
90.4% sorbitol;
1.8% anhydrous sodium carbonate;
0.3% sodium carboxymethylcellulose;
0.1% colloidal silicon dioxide;
0.6% glycine;
trace coloring; and
1.8% flavoring.
42. A dosage form as defined in claim 4, comprising:
5.0% azithromycin dihydrate;
46.3% sorbitol;
46.3% sucrose;
0.4% anhydrous tribasic sodium phosphate;
0.2% hydroxypropylmethylcellulose;
0.2% xanthan gum; and
trace coloring
1.8% flavoring.
43. A dosage form as defined in claim 4, comprising:
5.0% azithromycin dihydrate;
45.7% sucrose;
45.7% sorbitol;
0.9% anhydrous sodium carbonate;
0.2% anhydrous tribasic sodium phosphate;
0.1% hydroxypropylmethylcellulose;
0.1% xanthan gum;
0.1% sodium carboxymethylcellulose;
0.1% colloidal silicon dioxide;
0.3% glycine;
trace coloring; and
1.8% flavoring.
44. A dosage form as defined in claim 9, comprising:
9.5% azithromycin dihydrate;
88.2% sucrose;
0.8% anhydrous tribasic sodium phosphate;
0.5% colloidal silicon dioxide; and
0.9% flavoring.
45. A dosage form as defined in claim 9, comprising:
9.5% azithromycin dihydrate;
88.2% sorbitol;
0.8% anhydrous tribasic sodium phosphate;
0.5% colloidal silicon dioxide; and
0.9% flavoring.
46. A dosage form as defined in claim 9, comprising:
9.6% azithromycin dihydrate;
88.9% sucrose;
0.4% anhydrous tribasic sodium phosphate;
0.2% colloidal silicon dioxide; and
0.9% flavoring.
47. A dosage form as defined in claim 9, comprising:
9.3% azithromycin dihydrate;
86.1% sucrose;
1.8% anhydrous tribasic sodium phosphate;
2.0% colloidal silicon dioxide; and
0.9% flavoring.
48. A dosage form as defined in claim 9, comprising:
16.7% azithromycin dihydrate;
79.5% sucrose;
1.4% anhydrous tribasic sodium phosphate;
0.9% colloidal silicon dioxide; and
1.6% flavoring.
49. A dosage form as defined in claim 9, comprising:
9.5% azithromycin dihydrate;
44.1% sucrose;
44.1% sorbitol;
0.8% anhydrous tribasic sodium phosphate;
0.5% colloidal silicon dioxide; and 0.9% flavoring.

50. A dosage form as defined in claim 9, comprising:
9.5% azithromycin dihydrate;
44.1% sucrose;
44.1% sorbitol;
0.4% anhydrous tribasic sodium phosphate;
0.2% anhydrous sodium carbonate;
0.2% glycine;
0.5% colloidal silicon dioxide; and
0.9% flavoring.

51. A dosage form as defined in claim 14, comprising:
58.2% azithromycin dihydrate;
6.0% pregelatinized starch;
30.9% anhydrous dibasic calcium phosphate;
2.0% sodium croscarmellose; and
2.9% lubricant.

52. A dosage form as defined in claim 14, comprising:
58.2% azithromycin dihydrate;
11.1% pregelatinized starch;
25.7% anhydrous dibasic calcium phosphate;
2.0% sodium croscarmellose; and
2.9% lubricant.

53. A dosage form as defined in claim 14, comprising:
58.2% azithromycin dihydrate;
3.1% pregelatinized starch;
31.3% anhydrous dibasic calcium phosphate;
4.4% sodium croscarmellose; and
2.9% lubricant.

54. A dosage form as defined in claim 14, comprising:
58.2% azithromycin dihydrate;
11.1% pregelatinized starch;
23.3% anhydrous dibasic calcium phosphate;
4.4% sodium croscarmellose; and
2.9% lubricant.

55. A dosage form as defined in claim 14, comprising:
58.2% azithromycin dihydrate;
3.1% maize starch;
33.8% dibasic calcium phosphate, lactose, or microcrystalline cellulose;
2.0% sodium starch glycolate or crosslinked polyvinylpyrrolidone; and
2.9% lubricant.

56. A dosage form as defined in claim 14, comprising:
58.2% azithromycin dihydrate;
6.0% maize starch;
30.9% dibasic calcium phosphate, lactose, or microcrystalline cellulose;
2.0% sodium starch glycolate or crosslinked polyvinylpyrrolidone; and
2.9% lubricant.

57. A dosage form as defined in claim 14, comprising:
58.2% azithromycin dihydrate;
11.1% maize starch;
25.7% dibasic calcium phosphate, lactose, or microcrystalline cellulose;
2.0% sodium starch glycolate or crosslinked polyvinylpyrrolidone; and
2.9% lubricant.

58. A dosage form as defined in claim 14, comprising:
58.2% azithromycin dihydrate;
3.1% maize starch;
31.3% dibasic calcium phosphate, lactose, or microcrystalline cellulose;
4.4% sodium starch glycolate or crosslinked polyvinylpyrrolidone; and
2.9% lubricant.

59. A dosage form as defined in claim 14, comprising:
58.2% azithromycin dihydrate;
6.0% maize starch;
32.2% dibasic calcium phosphate, lactose, or microcrystalline cellulose;
0.7% sodium starch glycolate or crosslinked polyvinylpyrrolidone; and
2.9% lubricant.

60. A dosage form as defined in claim 14, comprising:
58.2% azithromycin dihydrate;
6.0% maize starch;
28.4% dibasic calcium phosphate, lactose, or microcrystalline cellulose;
4.4% sodium starch glycolate or crosslinked polyvinylpyrrolidone; and
2.9% lubricant.

61. A dosage form as defined in claim 17, comprising:
5.0% azithromycin dihydrate;
92.5% sucrose;
0.4% anhydrous tribasic sodium phosphate;
0.2% hydroxypropylcellulose;
0.2% xanthan gum;
trace coloring; and
1.8% flavoring.

62. A dosage form as defined in claim 17, comprising:
4.8% azithromycin dihydrate;
58.0% sucrose;
29.0% sorbitol;
1.9% anhydrous sodium carbonate;
0.4% sodium benzoate;
1.5% tragacanth gum powder;
1.5% titanium dioxide;
1.15% colloidal silicon dioxide;
0.6% glycine; and
2.3% flavoring.

63. A dosage form as defined in claim 17, comprising:
5.0% azithromycin dihydrate;
91.8% sucrose;
0.4% anhydrous tribasic sodium phosphate;
0.2% hydroxypropylcellulose;
0.2% xanthan gum;
0.1% colloidal silicon dioxide;
0.6% glycine;
trace coloring; and
1.8% flavoring.

64. A dosage form as defined in claim 17, comprising:
5.0% azithromycin dihydrate;
92.5% sucrose;
0.4% anhydrous tribasic sodium phosphate;
0.3% sodium carboxymethylcellulose;
trace coloring; and 1.8% flavoring.
65. A dosage form as defined in claim 17, comprising:
5.0% azithromycin dihydrate;
90.4% sorbitol;
1.8% anhydrous sodium carbonate;
0.3% sodium carboxymethylcellulose;
0.1% colloidal silicon dioxide;
0.6% glycine;
trace coloring; and
1.8% flavoring.
66. A dosage form as defined in claim 17, comprising:
5.0% azithromycin dihydrate;
46.3% sorbitol;
46.3% sucrose;
0.4% anhydrous tribasic sodium phosphate;
0.2% hydroxypropylmethylcellulose;
0.2% xanthan gum; and
trace coloring
1.8% flavoring.
67. A dosage form as defined in claim 17, comprising:
5.0% azithromycin dihydrate;
45.7% sucrose;
45.7% sorbitol;
0.9% anhydrous sodium carbonate;
0.2% anhydrous tribasic sodium phosphate;
0.1% hydroxypropylmethylcellulose;
0.1% xanthan gum;
0.1% sodium carboxymethylcellulose;
0.1% colloidal silicon dioxide;
0.3% glycine;
trace coloring; and
1.8% flavoring.
68. A dosage form as defined in claim 22, comprising:
9.5% azithromycin dihydrate;
88.2% sucrose;
0.8% anhydrous tribasic sodium phosphate;
0.5% colloidal silicon dioxide; and
0.9% flavoring.
69. A dosage form as defined in claim 22, comprising:
9.5% azithromycin dihydrate;
88.2% sorbitol;
0.8% anhydrous tribasic sodium phosphate;
0.5% colloidal silicon dioxide; and
0.9% flavoring.
70. A dosage form as defined in claim 22, comprising:
9.6% azithromycin dihydrate;
88.9% sucrose;
0.4% anhydrous tribasic sodium phosphate;
0.2% colloidal silicon dioxide; and
0.9% flavoring.
71. A dosage form as defined in claim 22, comprising:
9.3% azithromycin dihydrate;
86.1% sucrose;
1.8% anhydrous tribasic sodium phosphate;
2.0% colloidal silicon dioxide; and
0.9% flavoring.
72. A dosage form as defined in claim 22, comprising:
16.7% azithromycin dihydrate;
79.5% sucrose;
1.4% anhydrous tribasic sodium phosphate;
0.9% colloidal silicon dioxide; and
1.6% flavoring.
73. A dosage form as defined in claim 22, comprising:
9.5% azithromycin dihydrate;
44.1% sucrose;
44.1% sorbitol;
0.8% anhydrous tribasic sodium phosphate;
0.5% colloidal silicon dioxide; and
0.9% flavoring.
74. A dosage form as defined in claim 22, comprising:
9.5% azithromycin dihydrate;
44.1% sucrose;
44.1% sorbitol;
0.4% anhydrous tribasic sodium phosphate;
0.2% anhydrous sodium carbonate;
0.2% glycine;
0.5% colloidal silicon dioxide; and
0.9% flavoring.
75. A therapeutic package, comprising
a container,
an oral dosage form of azithromycin which exhibits either or both of:
 (a) at least about 90% dissolution of azithromycin within about 30 minutes when an amount of the dosage form equivalent to 200 mg of azithromycin is tested as set forth in USP test <711> in a USP-2 dissolution apparatus under conditions at least as stringent as the following: 900 ml sodium phosphate buffer, pH 6.0, 37° C., with paddles turning at 100 rpm; and/or
 (b) a value of $(AUC_{fed})/(AUC_{fst})$ of at least 0.80 with a lower 90% confidence limit of at least 0.75,
and, associated with said package, written matter non-limited as to whether the dosage form can be taken with or without food.
76. A therapeutic package as defined in claim 75, wherein said dosage form is in the form of a tablet.
77. A therapeutic package as defined in claim 75, wherein said dosage form is in the form of a powder for oral suspension.
78. A therapeutic package as defined in claim 77, wherein said dosage form is in the form of a suspension made from said powder.
79. A therapeutic package as defined in claim 75, wherein said dosage form is in the form of a unit dose packet.
80. A therapeutic package as defined in claim 79, wherein said dosage form is in the form of a suspension made from said unit dose packet.
81. A method for treating a microbial infection in a mammal which comprises administering, to a mammal that has eaten in need of such treatment, an antimicrobially effective amount of azithromycin in an oral dosage form which exhibits either or both of:
 (a) at least about 90% dissolution of azithromycin within about 30 minutes when an amount of the dosage form equivalent to 200 mg of azithromycin is tested as set forth in USP test <711> in a USP-2 dissolution apparatus under conditions at least as stringent as the following: 900 ml sodium phosphate buffer, pH 6.0, 37° C., with paddles turning at 100 rpm; and/or
 (b) a value of $(AUC_{fed})/(AUC_{fst})$ of at least 0.80 with a lower 90% confidence limit of at least 0.75.

82. A method as defined in claim 81, wherein said mammal is a human.

83. A method as defined in claim 82, wherein said dosage form exhibits a value of $(AUC_{fed})/(AUC_{fst})$ of at least 0.80 with a lower 90% confidence limit of at least 0.75.

84. A method as defined in claim 82, wherein said dosage form is in the form of a tablet.

85. A method as defined in claim 82, wherein said dosage form is in the form of a powder for oral suspension.

86. A method as defined in claim 85, wherein said dosage form is in the form of a suspension made from said powder.

87. A method as defined in claim 82, wherein said dosage form is in the form of a unit dose packet.

88. Method as defined in claim 87, wherein said dosage form is in the form of a suspension made from said unit dose packet.

89. A method as defined in claim 83, wherein said dosage form is in the form of a tablet.

90. A method as defined in claim 89, wherein said dosage form is in the form of a powder for oral suspension.

91. A method as defined in claim 90, wherein said dosage form is in the form of a suspension made from said powder.

92. A method as defined in claim 83, wherein said dosage form is in the form of a unit dose packet.

93. A method as defined in claim 92, wherein said dosage form is in the form of a suspension made from said unit dose packet.

94. A package as defined in claim 75, wherein said dosage form exhibits a value of $(AUC_{fed})/(AUC_{fst})$ of at least 0.80 with a lower 90% confidence limit of at least 0.75.

95. A package as defined in claim 94, wherein said dosage form is in the form of a tablet.

96. A package as defined in claim 94 wherein said dosage form is in the form of a powder for oral suspension.

97. A package as defined in claim 96, wherein said dosage form is in the form of a suspension made from said powder.

98. A package as defined in claim 94, wherein said dosage form is in the form of a unit dose packet.

99. A package as defined in claim 98, wherein said dosage form is in the form of a suspension made from said unit dose packet.

* * * * *